(12) United States Patent
Awtar et al.

(10) Patent No.: US 9,675,370 B2
(45) Date of Patent: *Jun. 13, 2017

(54) MINIMAL ACCESS TOOL

(71) Applicant: THE REGENTS OF THE UNIVERSITY OF MICHIGAN, Ann Arbor, MI (US)

(72) Inventors: Shorya Awtar, Ann Arbor, MI (US); Jens Nielsen, Traverse City, MI (US); Tristan Thomas Trutna, Atherton, CA (US); Andrew Mansfield, New Orleans, LA (US); Rosa Abani, Ann Arbor, MI (US); Patrick Quigley, Cassopolis, MI (US); James Geiger, Toledo, OH (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 415 days.

This patent is subject to a terminal disclaimer.

(21) Appl. No.: 14/166,503

(22) Filed: Jan. 28, 2014

(65) Prior Publication Data

US 2014/0142595 A1    May 22, 2014

Related U.S. Application Data

(63) Continuation of application No. 12/937,523, filed as application No. PCT/US2009/040353 on Apr. 13, 2009, now Pat. No. 8,668,702.

(Continued)

(51) Int. Cl.
*A61B 17/29* (2006.01)
*A61B 34/00* (2016.01)
(Continued)

(52) U.S. Cl.
CPC .......... *A61B 17/2909* (2013.01); *A61B 34/70* (2016.02); *A61B 34/71* (2016.02);
(Continued)

(58) Field of Classification Search
CPC ......... A61B 34/70; A61B 34/71; A61B 34/75; A61B 34/77; A61B 2034/306;
(Continued)

(56) References Cited

U.S. PATENT DOCUMENTS

| 3,497,083 | A | 2/1970 | Anderson et al. |
| 4,328,839 | A | 5/1982 | Lyons et al. |

(Continued)

FOREIGN PATENT DOCUMENTS

| GB | 0 973 587 A | 10/1964 |
| JP | 3-292879 A | 12/1991 |

(Continued)

OTHER PUBLICATIONS

Extended European Search Report for Application No. 09729763.4, dated Sep. 6, 2012.

(Continued)

*Primary Examiner* — Katrina Stransky
(74) *Attorney, Agent, or Firm* — Shay Glenn LLP

(57) ABSTRACT

A minimal access tool includes a frame arranged to be attached to an arm of a user, a tool shaft having a proximal end and a distal end, where the tool shaft proximal end is connected to the frame. The tool further includes an input joint having a first end connected to the frame and a second end arranged to receive user input, the input joint including a virtual center-of-rotation (VC) mechanism which provides a center of rotation that generally coincides with a wrist joint of the user. An output joint is connected to the tool shaft distal end, where the output joint is coupled to the input joint via a mechanical transmission connected therebetween to (Continued)

correlate motion of the input joint to motion of the output joint.

31 Claims, 10 Drawing Sheets

Related U.S. Application Data

(60) Provisional application No. 61/044,168, filed on Apr. 11, 2008.

(51) Int. Cl.
    *A61B 17/00*     (2006.01)
    *A61B 34/30*     (2016.01)

(52) U.S. Cl.
    CPC ............. *A61B 34/75* (2016.02); *A61B 34/77* (2016.02); *A61B 2017/00323* (2013.01); *A61B 2017/00424* (2013.01); *A61B 2017/00442* (2013.01); *A61B 2017/00464* (2013.01); *A61B 2017/2917* (2013.01); *A61B 2017/2929* (2013.01); *A61B 2017/2931* (2013.01); *A61B 2017/2937* (2013.01); *A61B 2017/2939* (2013.01); *A61B 2017/2944* (2013.01); *A61B 2034/306* (2016.02)

(58) Field of Classification Search
    CPC   A61B 2017/00323; A61B 2017/00424; A61B 2017/00442; A61B 2017/00464; A61B 2017/2917; A61B 2017/2929; A61B 2017/2931; A61B 2017/2937; A61B 2017/2939; A61B 2017/2944; A61B 17/2909; A61B 17/2841; B25J 13/02; B25J 13/00
    USPC .......................................................... 606/130
    See application file for complete search history.

(56) References Cited

U.S. PATENT DOCUMENTS

| | | | |
|---|---|---|---|
| 4,466,649 A | 8/1984 | Ozawa | |
| 4,568,311 A | 2/1986 | Miyake | |
| 4,712,545 A | 12/1987 | Honkanen | |
| 4,750,475 A | 6/1988 | Yoshihashi | |
| 4,754,909 A | 7/1988 | Barker et al. | |
| 4,950,273 A | 8/1990 | Briggs | |
| 5,021,969 A | 6/1991 | Okamura et al. | |
| 5,069,596 A | 12/1991 | Mueller et al. | |
| 5,147,357 A | 9/1992 | Rose et al. | |
| 5,209,747 A | 5/1993 | Knoepfler | |
| 5,297,443 A | 3/1994 | Wentz | |
| 5,317,952 A | 6/1994 | Immega | |
| 5,323,570 A | 6/1994 | Kuhlman et al. | |
| 5,330,502 A | 7/1994 | Hassler et al. | |
| 5,350,391 A | 9/1994 | Iacovelli | |
| 5,368,600 A | 11/1994 | Failla et al. | |
| 5,374,277 A | 12/1994 | Hassler | |
| 5,454,827 A | 10/1995 | Aust et al. | |
| 5,456,695 A | 10/1995 | Herve Dallemagne | |
| 5,549,637 A | 8/1996 | Crainich | |
| 5,599,151 A | 2/1997 | Daum et al. | |
| 5,620,415 A | 4/1997 | Lucey et al. | |
| 5,626,608 A | 5/1997 | Cuny et al. | |
| 5,683,412 A | 11/1997 | Scarfone | |
| 5,713,505 A | 2/1998 | Huitema | |
| 5,716,352 A | 2/1998 | Viola et al. | |
| 5,735,874 A | 4/1998 | Measamer et al. | |
| 5,782,748 A | 7/1998 | Palmer et al. | |
| 5,807,376 A | 9/1998 | Viola et al. | |
| 5,817,084 A | 10/1998 | Jensen | |
| 5,820,009 A | 10/1998 | Melling et al. | |
| 5,853,412 A | 12/1998 | Mayenberger | |
| 5,860,995 A | 1/1999 | Berkelaar | |
| 5,908,436 A | 6/1999 | Cuschieri et al. | |
| 6,270,453 B1 | 8/2001 | Sakai | |
| 6,309,403 B1 | 10/2001 | Minor et al. | |
| 6,312,435 B1 | 11/2001 | Wallace et al. | |
| 6,330,837 B1 | 12/2001 | Charles et al. | |
| 6,714,839 B2 | 3/2004 | Salisbury et al. | |
| 6,853,879 B2 | 2/2005 | Sunaoshi | |
| 6,889,116 B2 * | 5/2005 | Jinno ........................ | B25J 3/04 600/130 |
| 6,994,716 B2 | 2/2006 | Jinno et al. | |
| 7,043,338 B2 | 5/2006 | Jinno | |
| 7,101,363 B2 | 9/2006 | Nishizawa et al. | |
| 7,147,650 B2 | 12/2006 | Lee | |
| 7,314,472 B2 | 1/2008 | Jinno et al. | |
| 7,454,268 B2 | 11/2008 | Jinno | |
| 7,553,275 B2 | 6/2009 | Padget et al. | |
| 7,708,756 B2 | 5/2010 | Nobis et al. | |
| 7,736,254 B2 | 6/2010 | Schena | |
| 8,029,531 B2 | 10/2011 | Lee et al. | |
| 8,425,408 B2 | 4/2013 | Boulais et al. | |
| 8,465,475 B2 | 6/2013 | Isbell | |
| 8,528,440 B2 | 9/2013 | Morley et al. | |
| 8,540,748 B2 | 9/2013 | Murphy et al. | |
| 8,992,422 B2 | 3/2015 | Spivey et al. | |
| 9,220,398 B2 | 12/2015 | Woodley et al. | |
| 2001/0031983 A1 | 10/2001 | Brock et al. | |
| 2003/0036748 A1 | 2/2003 | Cooper et al. | |
| 2003/0135203 A1 | 7/2003 | Wang et al. | |
| 2003/0176880 A1 | 9/2003 | Long et al. | |
| 2003/0176948 A1 | 9/2003 | Green | |
| 2004/0023616 A1 | 2/2004 | Straub et al. | |
| 2004/0138700 A1 | 7/2004 | Cooper et al. | |
| 2004/0253079 A1 | 12/2004 | Sanchez | |
| 2005/0004431 A1 | 1/2005 | Kogasaka et al. | |
| 2005/0038469 A1 | 2/2005 | Lang | |
| 2005/0107667 A1 | 5/2005 | Danitz et al. | |
| 2006/0079865 A1 | 4/2006 | Jinno et al. | |
| 2006/0079866 A1 | 4/2006 | Jinno et al. | |
| 2006/0111210 A1 | 5/2006 | Hinman | |
| 2006/0111616 A1 | 5/2006 | Danitz | |
| 2006/0259073 A1 | 11/2006 | Miyamoto et al. | |
| 2006/0282063 A1 | 12/2006 | Gotani | |
| 2007/0021738 A1 | 1/2007 | Hasser et al. | |
| 2007/0078565 A1 | 4/2007 | Ghodoussi et al. | |
| 2008/0065098 A1 | 3/2008 | Larkin | |
| 2010/0004606 A1 | 1/2010 | Hansen et al. | |
| 2010/0030018 A1 | 2/2010 | Fortier et al. | |
| 2010/0056863 A1 | 3/2010 | Dejima et al. | |
| 2010/0234831 A1 | 9/2010 | Hinman et al. | |
| 2012/0041450 A1 | 2/2012 | Awtar et al. | |
| 2013/0012958 A1 | 1/2013 | Marczyk et al. | |
| 2016/0303734 A1 | 10/2016 | Bowles et al. | |

FOREIGN PATENT DOCUMENTS

| | | |
|---|---|---|
| JP | 8-84702 A | 4/1996 |
| JP | 2002102248 A | 4/2002 |
| JP | 2003061969 A | 3/2003 |
| JP | 2007130485 A | 5/2007 |
| WO | WO2006/036067 A2 | 4/2006 |
| WO | WO2007/146894 A2 | 12/2007 |
| WO | WO2008/020964 A2 | 2/2008 |

OTHER PUBLICATIONS

International Search Report from PCT/US2009/040353, mailed Nov. 17, 2009.

Written Opinion of the International Searching Authority from PCT/US2009/040353, mailed Nov. 17, 2009.

Japanese Office Action for Patent Application No. 2011-504234 Issued on Jun. 19, 2013.

Peirs et al.; A flexible distal tip with two degrees of freedom for enhanced dexterity in endoscopic robot surgery; MME'02; The 13th Micromechanics Europe Workshop; Sinaia, Romania; pp. 271-274; Oct. 6-8, 2002.

(56) References Cited

OTHER PUBLICATIONS

Simaan et al.; A dexterous system for laryngeal surgery; Proceedings of the 2004 IEEE International Conference on Robotics and Automation; New Orleans, LA.; pp. 351-357; Apr. 2004.
Awtar et al.; U.S. Appl. No. 15/054,068 entitled "Parallel kinematic mechanisms with decoupled rotational motions," filed Feb. 25, 2016.
Sharma et al.; U.S. Appl. No. 15/284,345 entitled "Handle mechanism providing unlimited roll," filed Oct. 3, 2016.
Licht et al.; U.S. Appl. No. 15/286,489 entitled "Medical devices having smoothly articulating multi-cluster joints," filed Oct. 5, 2016.
Zimmerman et al.; U.S. Appl. No. 15/286,547 entitled "End-effector jaw closure transmission system for remote access tools," filed Oct. 5, 2016.
Clement et al.; Design of a Snake-Like Manipulator; Robotics and Autonomous Systems; 6(3); pp. 265-282; Jul. 1990.
Ikuta et al.; Shape Memory Alloy Servo Actuator System With Electric Resistance Feedback and Application for Active Endoscope (conf. paper); 1988 IEEE Int'l Conf. on Robotics and Automation; pp. 427-430; Apr. 24-29, 1988.
Jug et al.; The JPL Serpentine Robot: a 12 DOF System for Inspection (Conference Paper); Proceedings—IEEE International Conference on Robotics and Automation 3: 5 pgs.; Jun. 1995.
Walker et al.; Novel 'Elephant"s Trunk' Robot; IEEE/ASME International Conference on Advanced Intelligent Mechatronics, AIM; Piscataway, NJ, United States; pp. 410-415; Sep. 19-23, 1999.
Wikipedia; Constant Velocity Joint; 6 pgs.; retrieved from the internet (htttps://en.wikipedia.org/wiki/Constant-velocity_joint) on Dec. 22, 2016.

\* cited by examiner

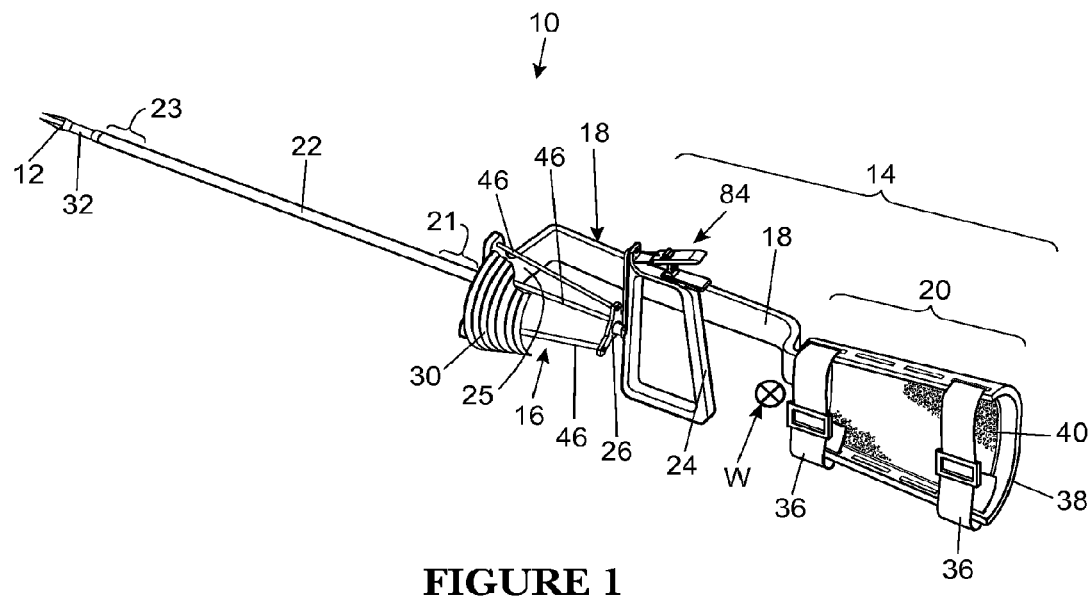
FIGURE 1
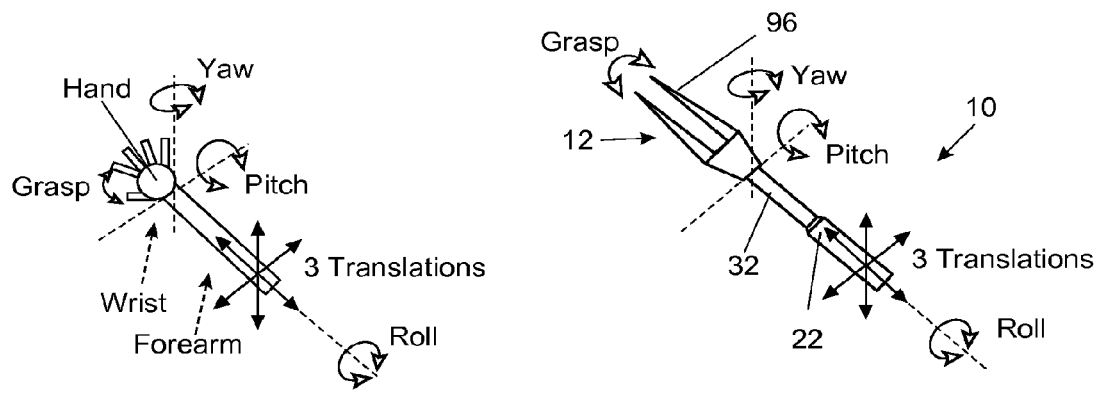
FIGURE 2a  FIGURE 2b

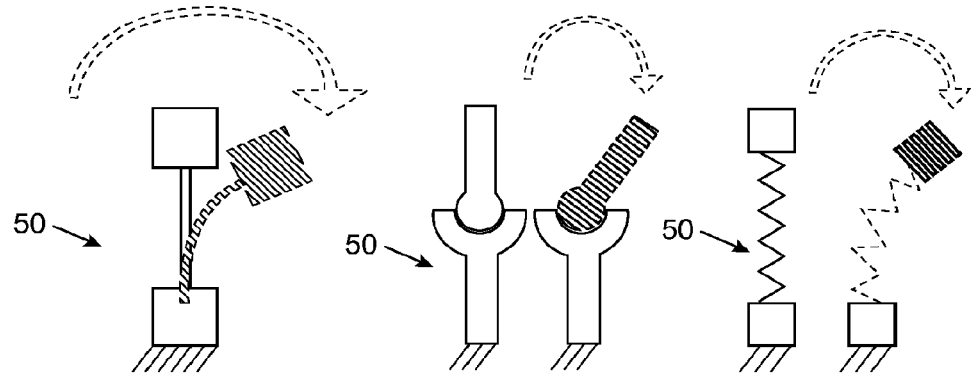
FIGURE 11a     FIGURE 11b     FIGURE 11c
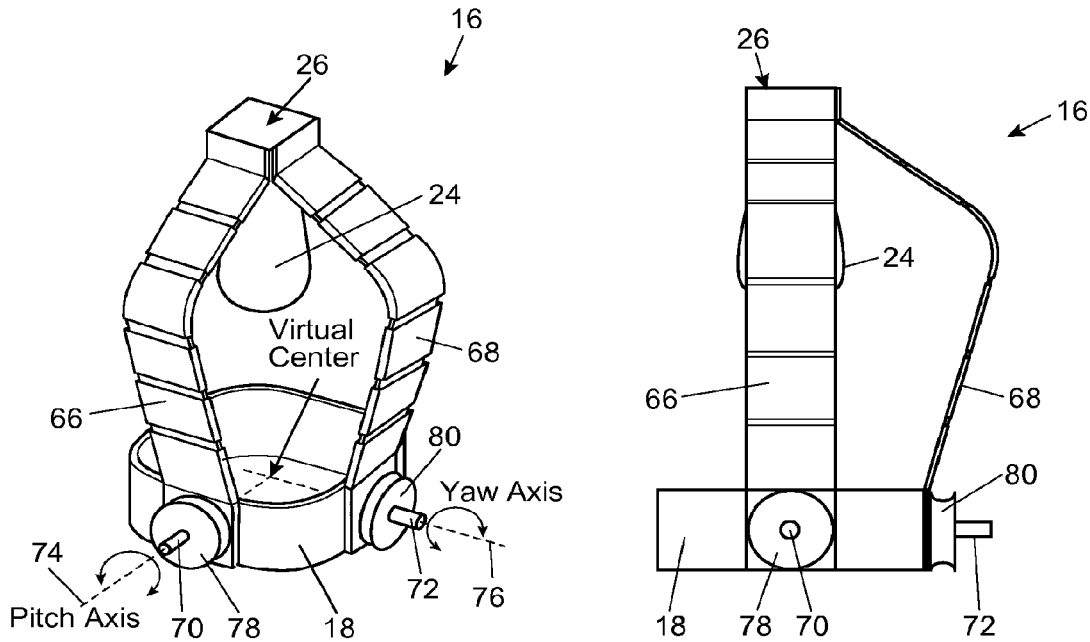
FIGURE 13a     FIGURE 13a

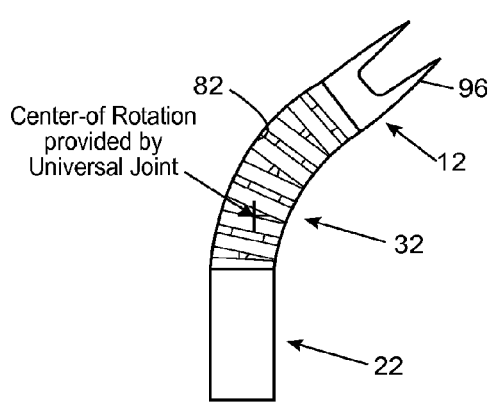
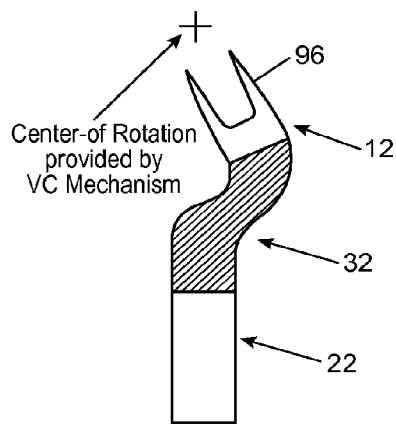
FIGURE 14a                FIGURE 14b
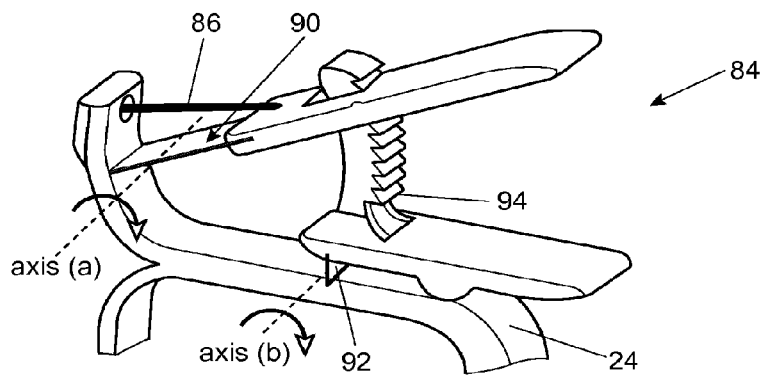
FIGURE 15

MINIMAL ACCESS TOOL

CROSS-REFERENCE TO RELATED APPLICATIONS

The present application is a continuation of U.S. patent application Ser. No. 12/937,523 filed Nov. 30, 2010, which is a US national phase application of International PCT Application No. PCT/US09/040353 filed Apr. 13, 2009, which claims the benefit of US provisional Application No. 61/044,168 filed Apr. 11, 2008. The entire text of each of the US and International PCT priority applications is incorporated herein by reference.

BACKGROUND OF THE INVENTION

1. Field of the Invention

This invention relates to a minimal access tool, such as for surgery, endoscopy, or other interventions.

2. Background Art

Minimally invasive surgical (MIS) and other minimal access procedures are increasing in frequency and becoming more complex, thus demanding improvements in technology to meet the needs of surgeons. In these procedures, generally thin tools are inserted into the body through ports. Motion input from the user, such as a surgeon, is transferred via the tool to the motion of a manipulator attached to the tool's tip inside the patient's body. This arrangement is used to carry out an externally controlled operation within the body without making large incisions. MIS tools range from simple scissor-like tools to complex robotic systems.

Most traditional tools for use in MIS are mechanical and hand-held, and provide 4 degrees of freedom (DoF) (3 translations and 1 roll rotation) plus grasping, while some newer ones further add up to 2 DoF (pitch, yaw). While these mechanical hand-held tools are inherently capable of force feedback, and the newer tools are capable of enhanced dexterity given their extra two DoF, they present non-intuitive DoF control (input motion to output motion mapping) schemes that limit user's ability to fully exploit the tool's enhanced dexterity capability. With robotic tools, the use of electromechanical actuators to produce motion of the tool tip manipulator takes away the mechanical force feedback. In addition, large size, high cost, and limited large-scale maneuverability also reduce the overall functionality of such robotic systems.

Therefore, most existing multiple DoF tools lack the design characteristics to allow for enhanced dexterity as well as desired functionality in a cost effective, compact package. In particular, multiple DoF tools that allow for wrist-like rotations of the tool tip manipulator are important to meet the needs of modern minimal access and MIS procedures, but are not effective unless comfortable, ergonomic, and intuitive control of these additional DoF are ensured.

BRIEF DESCRIPTION OF THE DRAWINGS

FIG. 1 is a perspective view of a minimal access tool according to the present invention;

FIGS. 2a and 2b are illustrations depicting the motion input at the user's end and motion output at the tool tip, respectively, of a minimal access tool according to the present invention;

FIGS. 11a, 11b, and 11c are schematic illustrations of compliant wire, ball-and-socket, and spring three DoF joints in accordance with the present invention;

FIGS. 13a and 13b are perspective and front elevational views, respectively, of a fixed axes VC mechanism according to the present invention;

FIGS. 14a and 14b are front elevational views of a cascaded-disk implementation and a VC mechanism implementation, respectively, of an output joint according to the present invention;

FIG. 15 is a perspective view of a closure mechanism according to the present invention;

DETAILED DESCRIPTION OF THE INVENTION

Figure 3:
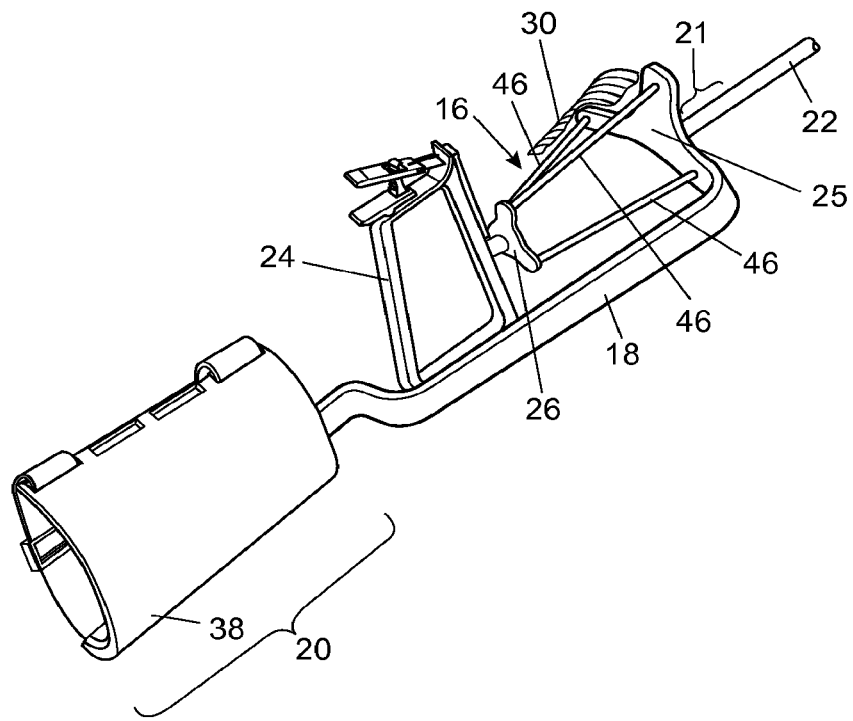
FIG. 3 is a perspective view of a user end of a minimal access tool according to the present invention.

As required, detailed embodiments of the present invention are disclosed herein; however, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

The present invention provides a high-dexterity, multi-DoF, minimal access tool capable of intuitive actuation for use in MIS, endoscopy, or other interventions. With reference to the drawings, a tool in accordance with the present invention is designated generally by reference numeral 10 and may provide the following functionality. First, six DoF may be provided at an end effector 12, such as a tool tip manipulator, to provide complete motion control in the three translational directions and three rotational directions. Additionally, the end effector 12 may have an open/close capability for grasping, cutting, etc., depending on its use. Ergonomic and intuitive motion mapping may be provided from an input (i.e., a user's arm, hand, and fingers) to an output (i.e., the end effector 12), and the tool 10 may provide force feedback to allow the user to feel the amount of force exerted by the tool 10. Still further, the tool 10 may provide motion scaling between the input and output motions, and hand-tremor reduction to improve the precision in surgery. It should be noted that "DoF" and "motion" are used interchangeably in the description provided herein. The tool 10 according to the present invention may be purely mechanical with a minimal number of components and assembly steps, ensuring simplicity and cost-effective manufacturing.

With reference to FIG. 1, a mechanical hand-held tool 10 is illustrated, wherein the DoF of the end effector 12 may be controlled by their physiological analogs at the user's end 14. Intuitive input-output motion mapping for the tool 10 may be achieved when the DoF motions of the end effector 12 match those of the user's arm, hand, and fingers. The tool 10 includes a frame 18 arranged to be attached to the user's arm, typically the forearm, such as via an arm attachment member 20 or other means. The frame 18 may be generally rigid, and also may incorporate length and size adjustability features so as to accommodate users of varying sizes. The tool 10 further includes a tool shaft 22 having a proximal end 21 and a distal end 23, wherein the frame 18 may be connected to the shaft proximal end 21. The tool shaft 22 is configured to pass through a surgical port in the patient's body (not shown), such that the tool shaft 22 may be generally elongated and thin with a generally round cross-section, although the shaft 22 is not limited to this configuration. The tool shaft 22 may be generally rigid, or alternatively a flexible tool conduit such as one used in endoscopy may be used while retaining all other functionality.

An input joint is connected to the frame 18 and arranged to receive the user's wrist motion input, wherein the input joint includes a virtual center-of-rotation (VC) mechanism 16 (best shown in FIGS. 9, 12, and 13) which provides a center of rotation that generally coincides with a wrist joint W of the user. In other words, the VC mechanism 16 creates a 2-DoF or 3-DoF joint with a virtual center-of-rotation located close to the user's own wrist W. A joint with a virtual center-of-rotation is one where no physical structure need exist at the virtual center-of-rotation. Such a joint should include a body that the user's hand can actuate, wherein this body is constrained by the VC mechanism 16 to move as if virtually pivoted at a point at the user's wrist by a 2-DoF universal or 3-DoF rotational joint. With this arrangement, the user's hand can rotate freely in at least two directions relative to the user's forearm naturally about the user's wrist W. The natural motion of the user's arm is then replicated at the end effector 12 inside the patient's body.

A traditional 2-DoF joint could be used for the input joint, as in U.S. Pat. No. 7,147,650, incorporated by reference herein. However, the center-of-rotation of the input joint in such cases coincides with the physical location of the joint, and hence can never be made to coincide with the user's wrist given the physical geometry/space constraints. Consequently, at the input the user would have to move his/her forearm, elbow, and shoulder along with the wrist to produce the output pitch and yaw motions at the end effector 12, which is cumbersome and non-intuitive. It is highly desirable for the user to be able to generate the pitch and yaw input motions by simply rotating his/her wrist relative to his/her forearm, which provides for the most natural, intuitive, and ergonomic actuation. For this to happen, the center-of-rotation of the input joint 16 should generally coincide with the location of the user's wrist. This enables the user to move his/her wrist naturally and comfortably during operation, independent of forearm, elbow, and shoulder motions.

Figure 9:
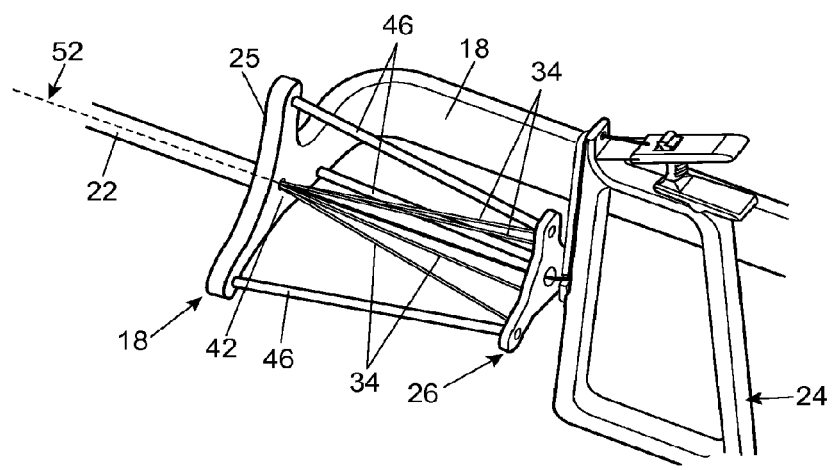
FIG. 9 is a perspective view of a tripod embodiment of a VC mechanism serving as an input joint of a minimal access tool according to the present invention.

With reference to FIGS. 1 and 3, the frame 18 gives structural integrity to the entire tool 10, providing a rigid connection between the arm attachment member 20 and the tool shaft 22, and also providing the reference ground for the VC mechanism 16. The frame 18 may be implemented in one of several ways. According to one non-limiting aspect of the present invention, a curved structure that does not interfere with the user's hand/fingers during wrist rotations may be provided, which may include a T-shaped or tubular cross-section to enhance structural rigidity. Also, as best illustrated in FIG. 9, the VC mechanism 16 may include a first end or ground base 25 which is connected to or part of the frame 18.

With further reference to FIG. 1, a second, input end of the VC mechanism 16 may comprise a floating member, such as a plate 26. The tool 10 may further comprise a handle 24 (also shown in FIGS. 3 and 4) mounted to the plate 26 to allow convenient grasping by a user's hand, wherein any wrist rotations of the user's hand are transmitted to the plate 26 via the handle 24. The handle 24 may include a soft covering comprised of a material such as rubber, and different types of grip tape, foam, or other materials may be used for comfort. The handle 24 may be of a pistol-grip type as depicted, or other handle shapes may be used including, but not limited to, scissor-like rings, a squeeze-ball grip design, or an ergonomic shape that conforms to a user's hand grip. Any shape of handle 24 may be used, provided it can be mounted to the floating plate 26. Alternatively, the handle 24 and the plate 26 may be embodied as a single component by simply extending the shape of the floating plate 26. It is also understood that the floating member 26 may take forms other than the plate depicted herein. The VC mechanism 16 may be covered with a baffle 30, such as for aesthetic reasons, and to contain an additional roll rotational DoF that may be provided by a 3-DoF VC mechanism 16 as described further below.

The end effector 12 may be connected to the tool shaft distal end 23 via an output joint 32, wherein the output joint 32 is mechanically coupled to the VC mechanism input joint 16 to correlate motion of the VC mechanism 16 to motion of the output joint 32. As such, the tool shaft 22 provides the reference ground for the end effector 12. A transmission system comprising cables 34 (best shown in FIGS. 5-10) connects the VC mechanism input joint 16 to the output joint 32 and end effector 12, thereby linking their motions. However, it is understood that the present invention is not limited to the use of cables 34, and that any type of mechanical transmission between the input joint 16 and the output joint 32 is fully contemplated. Furthermore, the dimensions and geometry of all components of the tool 10 according to the present invention may be chosen such that the wrist motion of the user's hand is replicated at the end effector 12 with any desired and adjustable scaling factor.

FIG. 2a shows the three translation motions and roll rotation of the human forearm, the two rotational motions (pitch and yaw) of the human wrist, and the grasping motion of human hand. FIG. 2b shows the corresponding DoF of the tool 10 according to the present invention. These DoF include three translations and a roll rotation of the tool shaft 22, two wrist-like rotations (pitch and yaw), and a grasping motion of the end effector 12. A tool 10 as described herein that provides a one-to-one mapping between the human input DoF and the output DoF of the end effector 12. The fact that the mapping of each DoF of the user input to the corresponding DoF of the end effector 12 is largely decoupled from the mapping of all the remaining DoF greatly facilitates the intuitive control (i.e., motion mapping from user input to tool output) of the end effector 12 by a user equipped with the tool 10.

In attaching the user's forearm to the tool shaft 22 via the frame 18 and the arm attachment member 20, and using the VC mechanism 16 in communication with the output joint 32, the 6 DoF of the arm and wrist, and the grasping action of the hand, may be relayed successfully to the end effector 12. Because control of the motion of the end effector 12 happens with natural motion of the user's forearm, wrist, and hand, the tool 10 according to the present invention successfully provides multi-DoF motion with intuitive input-output motion mapping. Because the system may be purely mechanical, it intrinsically relays force feedback.

In one embodiment, the roll rotation at the end effector 12 is the consequence of forearm roll rotation only, as there is no roll rotation at the user's wrist with respect to the user's forearm. Since the frame 18 is secured to the user's forearm, any roll rotation of the forearm is transmitted entirely to the frame 18, the tool shaft 22, and ultimately to the end effector 12 when the output joint 32 is a 2-DoF joint. Thus, it is acceptable to have an input joint 16 that provides three rotational DoF (the desired yaw and pitch, and an additional roll). The roll is redundant because, in the above-described arrangement, any roll DoF of the input joint 16 cannot be actuated by the user's wrist motion. For this actuation to happen, the wrist would have to roll with respect to the frame 18, but this cannot happen given the physiological construction of the human wrist. However, as explained here, if the input joint 16 is such that it provides an extra roll DoF, this DoF simply goes unused and has no detrimental effect of the desired functionality and dexterity of the overall tool 10.

In another embodiment, a spatial transmission mechanism may be used not only to transmit two rotational DoF (pitch and yaw) but all three rotational DoF (pitch, yaw, and roll). In such an embodiment, it would become possible to use input 16 and output 32 joints, each with three rotational DoF. In that case, the roll DoF of the input 16 and output 32 joints would be used.

The present invention provides a method to translate the user's forearm's four DoF (3 translations and one roll rotation) to the corresponding DoF of the end effector 12 by providing a reference ground for the end effector 12 that is rigidly attached to the user's arm. With reference to the description above of FIGS. 1-4, the tool 10 described herein may be provided with a continuous rigid structure attached directly or indirectly to the user's arm. This continuous rigid structure may also incorporate a relatively long narrow feature to penetrate the patient's body. The tip of the long narrow feature, which now is part of the continuous rigid structure, may provide a reference ground for the end effector 12. This ground and end effector 12 may be interconnected via an output joint 32. This continuous rigid structure also provides a reference ground for the VC mechanism 16 described above. The plate 26, which sees the user's motion inputs, may be connected to this ground via the VC mechanism input joint 16. Thus, the continuous rigid structure may effectively create a shared reference ground for the various mechanisms, sub-mechanisms, and joints in the tool 10 according to the present invention. This continuous rigid structure can include a single rigid body or several bodies connected rigidly to each other. These several rigid bodies may be detachable, re-attachable, and re-configurable.

According to one aspect of the present invention, the continuous rigid structure may comprise the arm attachment member 20, the frame 18, and the tool shaft 22 (see FIG. 1). The arm attachment member 20 may be used to attach the continuous rigid structure to the forearm of the user. The end effector 12 may be attached to the continuous rigid structure at the tool shaft distal end 23 via an output joint 32. During a surgical procedure, the end effector 12, the output joint 32, and a portion of the tool shaft 22 are generally in vivo, while the other components are generally in vitro. The implementation of the frame 18, the tool shaft 22, and the arm attachment member 20 dictates the general shape of the continuous rigid structure. Obviously, the geometries of these components and the overall continuous rigid structure can vary from that depicted herein and can be selected for right-hand or left-hand use.

In one embodiment, the end effector 12 may be made detachable so that the user may release and detach one end effector 12 and replace it with a different kind of end effector 12. The end effector 12 may be replaced while keeping the frame 18 attached to the user's forearm and the tool shaft 22 remaining attached to the frame 18. This allows the end effector 12 to be pulled out of the tool shaft 22 at a location outside the patient's body and be replaced by an end effector 12 with a different functionality during an operation, thus allowing the tool shaft 22 to remain in place while the end effector 12 is replaced. The end effector 12 and associated mechanisms may be disengaged utilizing a quick release or other mechanism and withdrawn through a hole in the frame 18 or tool shaft 22 without moving the tool shaft 22. This allows the user to change end effectors 12 while keeping the tool 10 inside of the patient.

Figure 4:
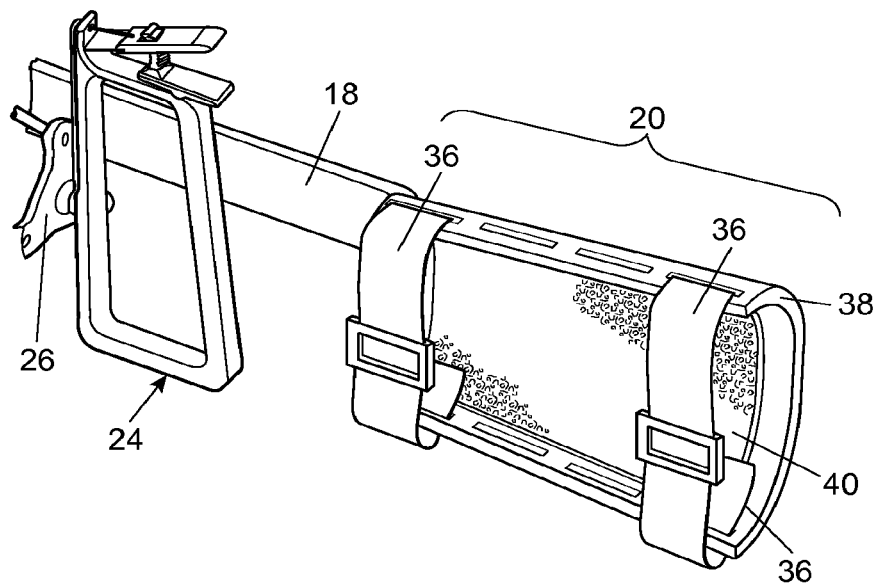
FIG. 4 is a perspective view of a user end of a minimal access tool according to the present invention including a forearm attachment device.

Turning to FIGS. 1 and 3-4, the arm attachment member 20 is provided to quickly and easily secure the user's forearm to the frame 18. The arm attachment member 20 may include flexible or rigid members to provide a secure interface between the forearm and the frame 18. According to one aspect of the present invention, the arm attachment member 20 may include flexible adjustable straps 36 that encircle the forearm and use a hook-and-loop arrangement, snap joints, buckles or other features for securing the arm attachment member 20 to the user's forearm. The arm attachment member 20 may also include a supporting shell-type structure 38 which may be made generally in the shape of a forearm (for example, half cone-shaped) to ensure comfort and correct attachment positioning. Furthermore, the shell structure 38 may be at least partially lined with a foam pad 40 or other suitable material to provide a comfortable interface between the user's forearm and the arm attachment member 20. The foam pad 40 may comprise a polyurethane open cell foam, although other types of soft gel and/or foam may also be used. In one embodiment, the arm attachment member 20 may extend around approximately half of the forearm circumference. According to one non-limiting aspect of the present invention, the arm attachment member 20 may be integrated with the frame 18 for ease of manufacturing.

It is understood that variations of the arm attachment member 20 are also contemplated within the scope of the present invention. For example, the support shell structure 38 may extend partially or completely around the forearm. If the shell structure 38 extends partially around the forearm, other flexible or rigid components may be used to completely enclose and secure the forearm. The shell structure 38 can also extend around the entire circumference of the arm either continuously or in multiple sections. If the shell structure 38 encircles the forearm continuously, shape-morphing padding may be used to fit the forearm in place snugly. This padding could possibly be either passive or actuated by pressure, heat, or some other controllable shape-morphing structure. If the shell structure 38 encircles the forearm in sections, joints may be provided between each section.

Figure 5A:
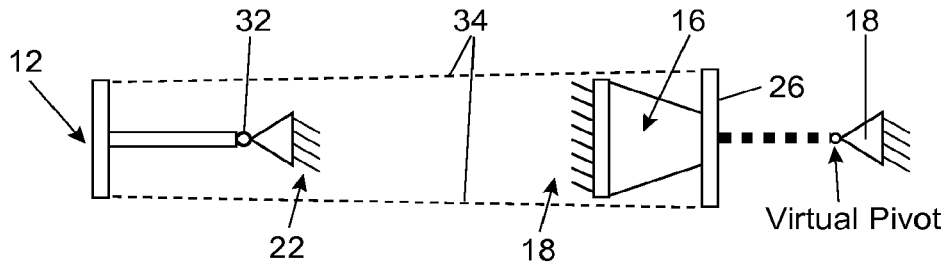
FIGS. 5a-5c are schematic illustrations of a cable transmission mechanism of a minimal access tool according to the present invention.
Figure 5B:
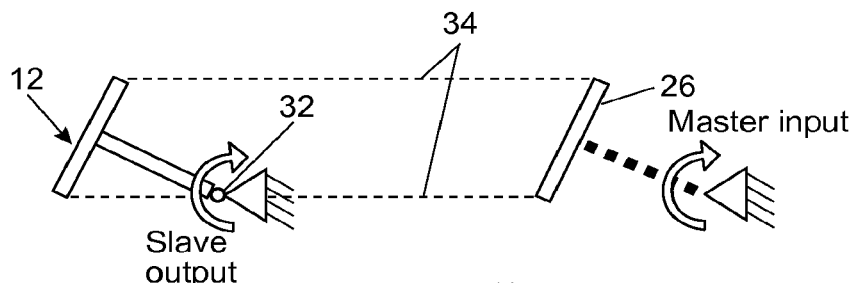
Figure 5C:
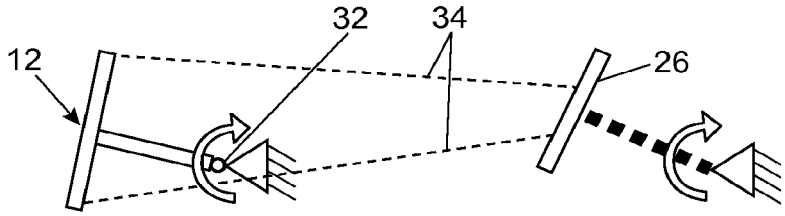

Turning now to FIGS. 5a-5c, the present invention provides a method to relate the two wrist DoF to the corresponding two rotational DoF of the end effector 12. This may be achieved using a master-slave, cable-based spatial transmission design, where the user actuates the master joint (input joint or VC mechanism 16) and the motion is transferred to the slave joint (output joint 32) via cables 34, and optionally cams (see, for example, FIG. 7) or pulleys (see, for example, FIG. 8). In this design, the two joints are coupled such that the motion at the output joint 32 is dependent on the input joint 16. The user input for actuating the input joint 16 comes from the rotation of the user's hand which happens about the user's wrist relative to the user's forearm. The two joints in question should have at least two rotational DoF (pitch and yaw) each. Furthermore, since the frame 18 is secured to the user's forearm, as described earlier, this structure also provides the ground for the two joints. Consequently, the two rotations produced at the end effector 12 are with respect to the user's forearm. A planar illustration of the transmission design, depicting one rotational DoF, is provided in FIG. 5 for the purpose of explanation. However, it should be understood that the present invention includes a spatial transmission design that transmits at least two wrist rotations (pitch and yaw) while utilizing 2-DoF or 3-DoF joints as the input 16 and output 32 joints.

In one embodiment, respective points on the floating plate 26 at the input joint 16 and the end effector 12 at the output joint 32 with similar orientation are connected (i.e., top to top, bottom to bottom, etc.) via cables 34, as schematically represented in FIG. 5. This kind of connection ensures independent control of the two rotational DoF at the end effector 12 by corresponding rotations of the user's wrist. Rotation of the input joint 16 causes push and/or pull action to be transmitted from the floating plate 26 to the end effector 12 via cables 34 that may pass through the tool shaft 22 and attach to the output joint 32. In general, corresponding points on the floating plate 26 and end effector 12 can be connected with either cables 34 or instead with rigid links (or push rods) with appropriate joints. It is also contemplated that the connection points could be reversed, e.g. top to bottom, bottom to top, to produce motion at the end effector 12 in a direction opposite the input motion at the floating plate 26 and the handle 24.

The transmission system according to the present invention allows for motion scaling, depending upon the type and location of the cable connection points. For example, FIG. 5c depicts motion scaling between the input and output joints 16, 32 which may be accomplished by varying the attachment points of the cables 34 between the end effector 12 (output joint 32) and the floating plate 26 (input joint 16). In one embodiment, compliant and dampened joints may be used in the VC mechanism 16, a compliant and dampened universal joint may be used for the output joint 32, and finite stiffness cables 34 may be used for the motion transmission system. All these flexible and dampening elements together may act as a low-pass filter, reducing the effects of high frequency input hand-tremors at the output motion of the end effector 12.

Figure 6:
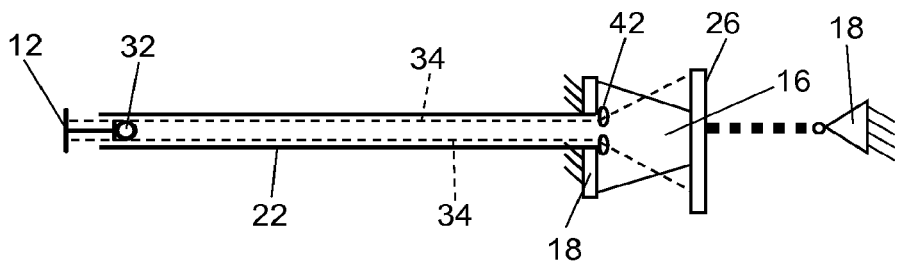
FIG. 6 is a schematic illustration of another embodiment of a cable transmission mechanism of a minimal access tool according to the present invention.
Figure 7:
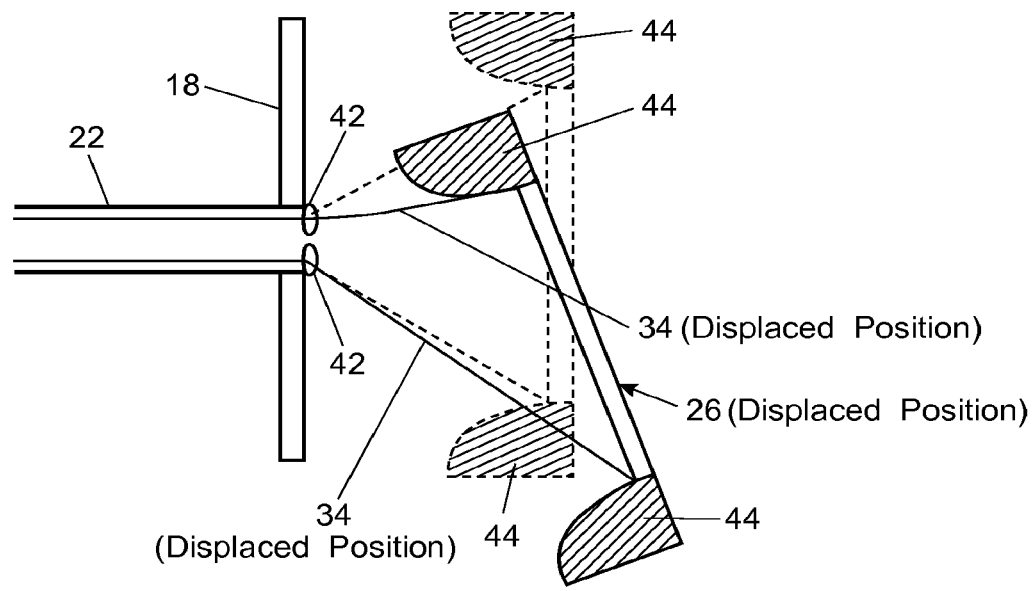
FIG. 7 is a schematic illustration of an input of a cable transmission system according to the present invention in the presence of cam surfaces.
Figure 8:
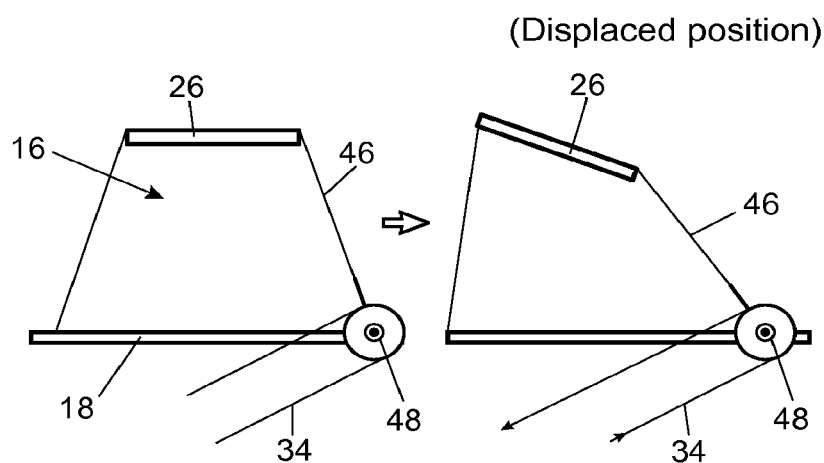
FIG. 8 is a schematic illustration of a cable transmission system according to the present invention wherein the transmission cables are attached to links of a virtual center-of-rotation (VC) mechanism.

The cables 34 may be routed through the tool shaft 22 (e.g., as illustrated in FIGS. 6 and 7) so that they remain shielded and protected from wear. According to the present invention, there may also be several routing components to prevent tangling of the cables 34 and ensure uninhibited motion. These components may be attached to the frame 18 or the tool shaft 22, and may include several individual holes 42 through which individual cables 34 pass. There may be variations on these routing components, depending on the configuration of the tool shaft 22 and the frame 18.

With the motion transmission system according to the present invention, a plurality of cables 34 may be used such as, but not limited to, four or more. Increasing the number of cables 34 may be beneficial up to a certain point, providing a higher degree of articulation at every position. The cables 34 may also be stiff or moderately compliant along their lengths. If compliant, the cables 34 may have inherent flexibility or springiness in series that provide the elasticity. This axial compliance can be carefully selected to filter/dampen any hand tremors and provide more stable and precise motion at the end effector 12.

At least one spring or other such mechanism may be attached to the VC mechanism 16 ground (i.e., the frame 18) on one side and the floating plate 26 on the other side. While such a spring would not constrain the previously described DoF of the input joint 16, it may keep the plate 26 in a nominal "centered" condition in the lack of any input motions from the user.

As shown in FIG. 7, as the plate 26 of the VC mechanism 16 turns to one side in response to a user input at handle 24, it pulls on the transmission cable 34 on one side and releases the transmission cable 34 on the other side. The tension in the cable 34 on one side transmits all the way to the end effector 12 and makes it turn accordingly. During this entire procedure, the geometry of the VC mechanism 16 and transmission may be such that more cable 34 is released on the second side as compared to the amount of cable 34 pulled on the first side. Since the overall length of cable 34 has to remain constant in the system, this results in cable slack on the second side. According to one embodiment, cam surfaces 44 may be incorporated in the floating plate 26 geometry, another portion of the input joint 16, or the frame 18 in order to alleviate this issue. It is understood that cam surfaces 44 may be utilized in any of the various tool embodiments disclosed herein. The cam surfaces 44 may be configured such that any extra cable 34 on any side of the input portion of the transmission gets wrapped over the cam surface 44, thus effectively eliminating any cable slackness. Another embodiment, illustrated in FIG. 8, involves attaching the transmission cables 34 to one or more components/links of the VC mechanism 16 as opposed to the floating plate 26 of the VC mechanism 16. Pulleys 48 may also be utilized, wherein each pulley 48 rotates about a point on the frame 18 and alleviates the challenges associated with cable slack discussed above.

Turning now to FIG. 9, an embodiment of the VC mechanism 16 which includes a tripod linkage mechanism is illustrated. This tripod mechanism may include two plates 25, 26 and three rigid links 46. Each link 46 may be connected to the plates 25, 26 on either end via joints 50, such as those depicted in FIG. 11. Of the two plates 25, 26, plate 25 provides the mechanism ground, and in this case is part of the frame 18. The other plate 26 constitutes the floating member of the VC mechanism 16, which in turn attaches to the handle 24. One end of each link 46 may be attached in approximately 120 degree (measured with respect a longitudinal tool axis 52) increments to the frame 18, while the other end of each link 46 may be similarly attached to the plate 26 at a smaller radius but approximately the same degree increments. The relative radius of attachment between the two plates 25, 26 determines the location of the virtual center of location, as illustrated in FIG. 10.

Figure 10:
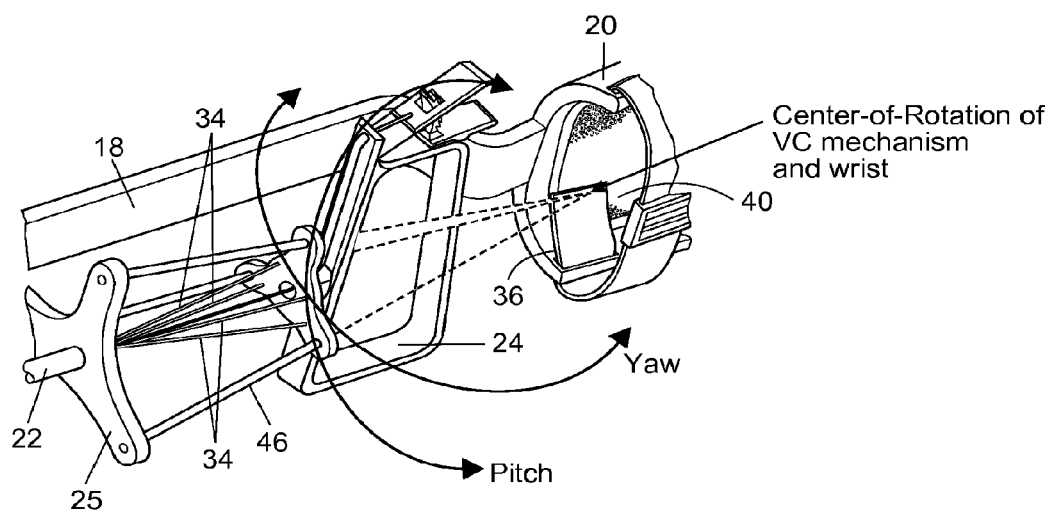
FIG. 10 is a perspective view of an input joint center-of-rotation provided by a tripod mechanism according to the present invention as it coincides with a user's wrist.

In mounting the links in this manner, the three axes that extend axially through each link 46 intersect generally at the user's wrist location (FIG. 10). The intersection of these axes is also the center-of-rotation of the VC mechanism 16, and therefore the input joint. Thus, the input joint's center-of-rotation is made to coincide with the user's wrist. As a result, when the plate 26 is moved from its nominal position, it moves along a trajectory that lies approximately on a sphere centered at the user's wrist. Therefore, if the user's hand holds the floating plate 26, natural wrist rotation (pitch and yaw) is allowed. Note that, in accordance with the present invention, the VC location could be adjusted by varying the connection points of the links 46 on either of the two plates 25, 26. Alternately, the connection points could be kept fixed while the lengths of the individual links 46 may be made variable. Either of these two options allow adjusting the tool 10 to fit a range of user hand sizes and comfort. Similar VC mechanisms 16 may be realized by using four, five, or more rigid links 46, instead of the three links 46 shown, arranged such that all links 46 when extrapolated in the undeformed/nominal condition meet at the same point, which would be the mechanism's virtual center-of-rotation.

The rigid links 46 used in the above-described embodiments can be any shape, and the joints 50 between the links 46 and the plates 25, 26 may be implemented in various different ways. The links 46 may be of circular, square, hexagonal, or any other cross-section, and may also be solid or hollow. In another embodiment, the links 46 may be replaced with continuous semi-rigid wires, such as piano wire, that are axially inextensible but are compliant in bending and torsion. In yet another embodiment, one could use links 46 that are compliant in bending and tension, as well as axial directions.

As illustrated in FIG. 11, the joints 50 may be joints of one of several different kinds including, but not limited to, a compliant wire (FIG. 11a), a traditional ball-and-socket joint assembly (FIG. 11b), a coiled extension spring (FIG. 11c), and others. Coiled extension springs provide some additional elasticity in the axial direction, which a traditional ball and socket joint does not. This added axial elasticity may extend the allowable range of motion of the VC mechanism 16. As the user moves the floating plate 26 away from its undeformed/nominal condition, the plate 26 and attached handle 24 pull away from the user's hand due to the kinematics of the tripod mechanism. When coiled springs are used, they can stretch axially and allow the user to move the handle 24 freely, providing a greater deflection. Coiled springs may make the tool 10 according to the present invention more robust, minimizing the need for maintenance and chances of failure.

In accordance with the present invention, other possible mechanisms to create a virtual center at the wrist may include any other linkage mechanism with any number of rigid or compliant links wherein the trajectory of one (floating) link is generally restricted to motion on the surface of a sphere (2 DoF rotation) centered at the wrist.

As described above, the VC mechanism 16 may include a floating plate 26 that the user's hand can actuate, such as via a handle 24, with respect to the frame 18. The VC mechanism 16 ensures that this plate 26, and therefore the handle 24, is restricted to move as if virtually pivoted around a point at the user's wrist via a 2 DoF or 3 DoF joint. The VC mechanism 16 should provide a virtual center located at the user's wrist as best as possible. Second, the virtual center created by the VC mechanism 16 should remain located close to the user's wrist throughout the mechanism's entire range of motion. However, the VC mechanism 16 may cause a drift in the location of the virtual center, typically with large rotational displacements by the user. In certain embodiments of the VC mechanism 16, the location of the virtual center can drift along the axis of the tool 10, which is a consequence of the mechanism type and geometry. Dimensions and geometry can be chosen to minimize the magnitude of this drift, but a small amount may remain. In that case, it is desirable that the VC mechanism 16 provide some means for accommodating the deviation of the virtual center from the user's actual wrist rotation point (such as the springs described above). If this is not provided, the range by which the user can move the plate 26, via the handle 24, smoothly and effortlessly in the yaw and pitch rotational directions may become restricted.

Figure 12A:
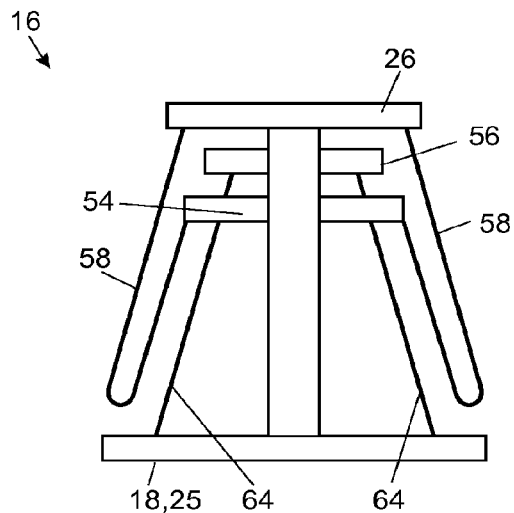
FIGS. 12a, 12b, and 12c are front elevational, side elevational, and perspective views, respectively, depicting a cascaded-link VC mechanism according to the present invention.
Figure 12B:
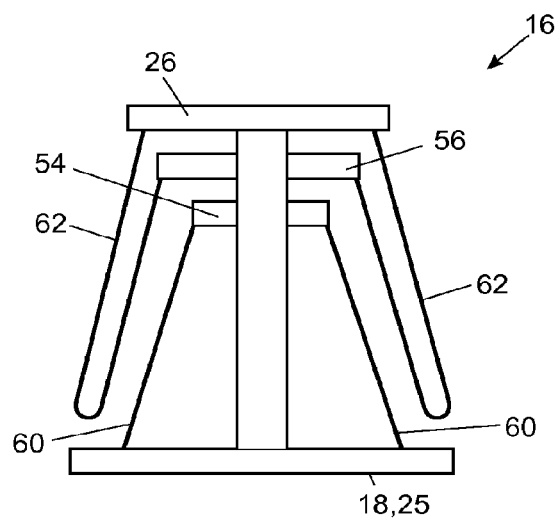
Figure 12C:
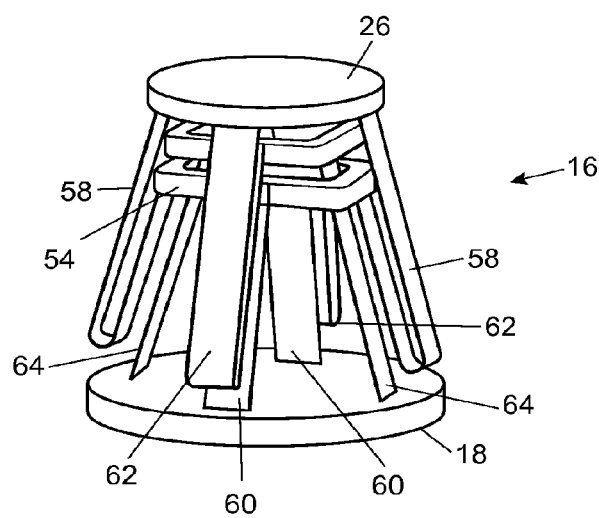

The VC mechanism 16 should allow for a practical transmission method to transmit the floating plate 26 pitch and yaw motions, actuated by the user's hand via the handle 24, to the end effector 12. In another embodiment, a cascaded VC mechanism 16 may be provided which resolves the user input (which can be a general combination of pitch and yaw) and into two clearly separated single rotations. In other words, as depicted in FIGS. 12a-12c, when the floating plate 26 is rotated by yaw and pitch, a first intermediate member or plate 54 only experiences the yaw part of the overall input motion while rejecting the pitch component, whereas a second intermediate member or plate 56 only experiences the pitch part of the overall motion while rejecting the yaw component. Cables (not shown) mechanically coupled to the first and second intermediate members 54, 56 then transmit the separate pitch and yaw motions to the end effector 12. Cam surfaces, similar to those described above with reference to FIG. 7, may be provided on one or both of the first and second intermediate members 54, 56 in order to prevent cable slack. This configuration reduces the one 2-DoF transmission design problem, which has to transmit two rotations at the same time, into two 1-DoF transmission design problems, each of which have to transmit only one rotation independent of the other.

The floating plate 26 of the VC mechanism 16 may be connected to the intermediate member 54 via a first set of connectors 58. Connectors 58 may be such that they transmit a yaw rotation from the floating plate 26 to the first intermediate member 54 because the connectors 58 are stiff in that direction. The first intermediate member 54 may be connected to the frame 18 via a second set of connectors 60. Because the connectors 58 are compliant in the pitch direction and the connectors 60 are stiff with respect to pitch rotation relative to the frame 18, any pitch rotation of the floating plate 26 does not get transmitted to the first intermediate member 54.

Thus, this VC mechanism 16 provides a mechanical filtering arrangement such that, given any random combination of yaw and pitch rotations of the plate 26 (actuated by the user's hand such as via the handle 24), only the yaw component of that rotation is seen by the first intermediate member 54, while the pitch component of the overall rotation is rejected or not seen by the first intermediate member 54. In the other direction, the plate 26 is attached to the second intermediate member 56 via a third set of connectors 62 which are stiff in the pitch direction and compliant in the yaw direction. The second intermediate member 56 is attached to the frame 18 via a fourth set of connectors 64 which are stiff in the yaw direction and compliant in the pitch direction. Hence, any pitch rotation of the floating plate 26 is transmitted to the second intermediate member 56 via the connectors 62. However, any yaw rotation of the plate 26 is not transmitted to the second intermediate member 56 since the connectors 62 are compliant in this direction and the connectors 64 are stiff in this direction.

In the end, therefore, this embodiment of the VC mechanism 16 is able to separate out the combined yaw and pitch rotations of the floating plate 26 into a pure yaw rotation of the first intermediate member 54 and a pure pitch rotation of the second intermediate member 56. Now, intermediate members 54, 56 may be used to further transmit the yaw and pitch rotations to the end effector 12 via coupling to cables (not shown). As mentioned above, two relatively independent 1-DoF transmission problems may be dealt with as opposed to a single 2-DoF transmission problem. It should be noted that the members 54, 56 and connectors 58, 60, 62, and 64 are not limited to the shapes and configurations depicted herein.

Connectors 60 and 64 may be oriented such that an extrapolation of their lengths would intersect at the user's wrist. This may provide the virtual center attribute of the VC mechanism 16. Connectors 58 and 62 may be shaped such that they do not impose any constraint along the tool axis 52. Thus, any deviation of the virtual center provided by connectors 60 and 64 from the actual wrist center of the user may be accommodated by the axial direction compliance of connectors 58 and 62.

Turning now to FIGS. 13a and 13b, a fixed axes VC mechanism 16 is shown. This VC mechanism 16 provides a method to transmit the pitch and yaw rotations about the respective fixed axes, actuated by the user's hand via the handle 24, to the end effector 12. This may be accomplished by resolving the user input (which can be a general combination of pitch and yaw) into two clearly separated single rotations about their fixed respective axes. The VC mechanism 16 includes two fixed orthogonal pivots whose extended lines of rotation intersect, and thus create a virtual center, at the location of the user's wrist. This VC mechanism 16 ensures that the handle 24, and therefore the user's hand, is allowed to move as if virtually pivoted about a point located at the user's wrist. It should be noted that the handle 24 in this embodiment can move in towards or out away from the arm attachment location, allowing the tool 10 to naturally adapt to a wide range of user hand and arm sizes, and ensuring that there is no restriction to the natural range of motion of the user's wrist.

Referring again to FIGS. 13a and 13b, the handle 24 and the floating plate 26 may be connected to a first, pitch connector 66 and a second, yaw connector 68 as shown. Each connector 66, 68 may in turn be pinned about a shaft 70, 72 on the respective pitch 74 and yaw 76 axes, wherein the pitch shaft 70 may receive a pitch axis pulley 78 and the yaw shaft 72 may receive a yaw axis pulley 80. The shafts 70, 72 are connected to the frame 18, which is secured to the user's arm, such that the rotations are relative to the VC mechanism 16 itself. The pitch connector 66 is stiff about the pitch axis, but is compliant about the yaw axis, allowing for the transmission of only the pitch component of the rotation while filtering the yaw component by allowing unconstrained rotation of the pitch connector 66 about the yaw axis. The opposite is true for the yaw connector 68, which will strictly transmit any yaw component of rotation while it will reject any pitch component of rotation. This design reduces the one 2-DoF transmission design problem, which has to transmit two rotations at the same time, into two 1-DoF transmission design problems, each of which have to transmit only one rotation independent of the other, such that the motion and force inputs about fixed axes may be easily transmitted to the end effector 12. Most importantly, the resulting virtual center location remains static with respect to the tool frame 18 (and therefore the user's forearm) at all times.

As such, this fixed axes VC mechanism 16 provides a mechanical filtering arrangement such that, given any general combination of yaw and pitch rotations to the handle 24 via the user's hand, only the yaw component of that rotation is seen by the yaw connector 68 while the pitch component of the overall rotation is rejected and not experienced about the yaw axis 76, and only the pitch component is seen by the pitch connector 66 while the yaw component is rejected and not experienced about the pitch axis 74. In the end, the combined yaw and pitch rotations of the handle 24 may be separated into a pure yaw rotation about the yaw axis 76 and a pure pitch rotation about the pitch axis 74. Now, the rotations about the respective pitch and yaw axes 74, 76 may be used to transmit the desired yaw and pitch rotations to the pitch and yaw axes of the end effector 12. In particular, the rotations produced at the pitch and yaw axis pulleys 78, 80 may be individually transmitted to the end effector 12 using a cable arrangement (not shown) similar to the one described above.

With this fixed axes embodiment, the orthogonal pitch and yaw axes of rotation intersect at the location of the wrist, providing the desired VC mechanism 16 behavior. In addition, since the axes are fixed, the location of the virtual center will remain stationary throughout the range of motion of the VC mechanism 16. The geometry of the connectors 66, 68 is such that they do not impose any constraint along the tool axis 52 (see FIG. 9), allowing for handle 24 adjustability by the user. Lastly, the fixed axes of rotation provide a trivial transmission method that can independently transmit pitch and yaw components of a rotational input by the user to the end effector 12 while maintaining a constant transmission cable length.

In one embodiment, the present invention provides a 2 DoF (pitch and yaw) output joint 32 for motion output at the end effector 12. The output joint 32 transmits roll rotation from the tool shaft 22 to the end effector 12. Since the tool shaft 22 is part of the continuous rigid structure, and since the continuous rigid structure is secured to the user's forearm, the roll rotation of the user's forearm can be transmitted to the end effector 12. Therefore, a 2-DoF rotational joint, that provides pitch and yaw rotation DoF, mounted to the in vivo portion of the tool shaft 22 may be used for this purpose. In another embodiment, the output joint 32 may be provided with a third DoF (roll rotation), along with an appropriate method for actuating this roll rotation by the user at the tool's input end 14.

According to one embodiment of the present invention, as illustrated in FIG. 14*a*, the output joint 32 may be a flexible, snake-like joint, such as one comprising flexible disks 82 attached in a fashion such that the direction of flexure of each element alternates. This joint 32 can be actuated by pushing or pulling on the disks 82 in different places, causing expansion and contraction of its sides. Cables (not shown) running through each disk 82 of the output joint 32 may be selectively pulled to create deflection in the yaw and pitch rotation directions or any combination thereof. Alternative joint types that could be used include, but are not limited to, inextensible wire compliant in bending, hourglass flexure, compression/extension springs with constrained torsion, or any other 2-DoF (yaw and pitch) joints. It is also contemplated that the output joint 32 may be temporarily locked in any desired orientation with respect to the tool shaft 22.

Instead of being a traditional 2-DoF joint, the output joint 32 may also be realized by means of a VC mechanism as illustrated in FIG. 14*b*, similar in intent to the one used at the input joint 16 described above. Barring space constraints, such a VC mechanism at the output joint 32 provides a center-of-rotation for the end effector 12 that can be conveniently located at any location other than the physical location of the output joint 32.

The present invention also provides a method to relate a user's grasp (from thumb/fingers) to the end effector 12. A grasping motion of the end effector 12 may be actuated via a cable system that passes from the handle 24 to the end effector 12. In one embodiment, the input motion device may comprise a lever 84 mounted on the handle 24 that is mechanically coupled to the end effector 12 for actuating a grasping motion of the end effector 12. More particularly, a cable 86 may be attached to the lever 84 and an associated closure mechanism 88 provided, wherein the cable 86 may transmit the grasping motion from the lever 84 and the closure mechanism 88 to the end effector 12. The grasping transmission system transmits one grasping DoF from the user's thumb/fingers to a corresponding open/close action (also one DoF) at the end effector 12. Since the handle 24 will move along with the user's hand, thumb and fingers during wrist motion, providing the lever 84 and the closure mechanism 88 on the handle 24 ensures that the input device for providing the grasping motion does not move relative to the hand, thumb, and fingers.

Referring to FIG. 15, as the user's thumb presses the lever 84 it rotates approximately about axis (a). A flexure element 90, such as a piece of spring steel, may be used as a one-DoF joint, wherein this joint may be compliant in nature so as to automatically return to its nominal (undeformed) position. This automatic return is desirable to ease the motion input requirements for the user's thumb. It is understood that any one-DoF joint could be used for this actuation, for example, a pin, slider, or push button (compliant or spring-mounted), provided one end is mounted to the handle 24 and the other is acted on by the fingers or thumb. Using thumb actuation allows the user to grasp the handle 24 with their fingers and palm while independently actuating the lever 84. A finger-actuated lever could alternatively be used, depending on size constraints from the shape of the handle 24.

According to one non-limiting aspect of the present invention, the closure mechanism 88 may include a ratcheting mechanism which allows the user to lock the lever 84 in different positions. This device may also use a compliant one DoF flexure joint 92 as shown in FIG. 15. The ratcheting mechanism is similar to those seen in U.S. Pat. Nos. 5,209,747 and 4,950,273, incorporated by reference herein, and may comprise a toothed body 94 that engages a single tooth on the lever 84 in different positions. As the user depresses the lever 84, the toothed body 94 deflects about axis (b) and allows the lever 84 to slip down to the next tooth. When the user releases the lever 84, it remains at whatever current position it is in. To release the lever 84, the toothed body 94 is simply deflected forward by the user's thumb causing the ratchet teeth to disengage. The springiness of the flexure joint 92 holding the lever 84 causes the lever 84 to go back to its nominal condition. In general, any other variable closure mechanism may be used instead of the ratcheting mechanism, depending on the specifics of the application. Such a mechanism provides the user the ability to hold a grasp (for example, on a tissue) inside the patient's body via the jaws 96 of the end effector 12.

During operation, the handle 24 moves along with the user's hand and wrist, such that the distance between the user input and the tool output is variable. Because each user input motion should be independent for the desired tool functionality, a transmission means that allows for a variable distance and orientation between components is generally desirable. In the system of FIG. 15, relative motion between the cable 86 and a sheath (not shown) may be used for actuation. The 86 cable may attach to the end effector 12, pass through the tool shaft 22, pass through the sheath to the floating plate 26 of the VC mechanism 16, pass through the handle 24, and then attach to the lever 84. The sheath may be connected between the tool frame 18 and the plate 26. Between the tool frame 18 and the plate 26, there may be slack in the sheath to ensure that the motion of the plate 26 is not constrained by the sheath. When the floating plate 26 moves in response to user wrist actuation, the amount of slack in the sheath will change but there will be no relative motion between the cable 86 and sheath.

The sheath through which the transmission cable 86 runs between the tool frame 18 and floating plate 26 can be any type of hollow body that is flexible in bending. According to one non-limiting aspect of the present invention, the sheath may include a flexible coiled spring or nylon tubing that provides enough flexibility in bending, but has a high stiffness under compression. This stiffness ensures that the relative motion between the cable 86 and the sheath dominate during tension in the transmission cable 86. When the cable 86 is pulled through the sheath, the cable 86 acts the same regardless of the shape of the sheath. With slack introduced in the sheath, the cable 86 can be straightened for a certain distance and without the grasping actuation force in the cable 86 being affected. This cable/sheath system may be implemented in various ways, but ultimately should allow for a variable distance between the tool frame 18 and the floating plate 26 of the VC mechanism 16. It should be noted that such a cable/sheath arrangement may be used not only for the grasping action transmission, but also for the transmission of the wrist rotations from the input joint 16 to the output joint 32. For example, separate sheaths could be employed for two pitch transmission cables, two yaw cables, and one grasping actuation cable.

Figure 16:
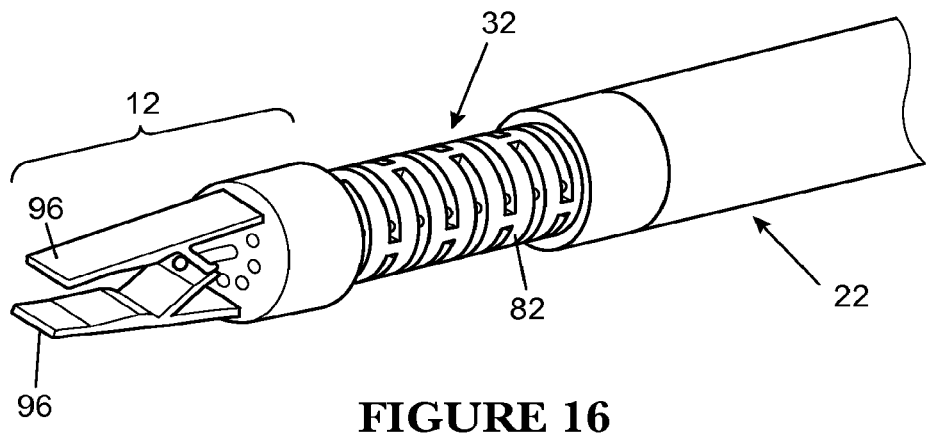
FIG. 16 is a perspective view of an end effector according to the present invention.

As described above, the end effector 12 reproduces the user's actions in vivo. The end effector 12 can be any number of one DoF devices, such as scissors, shears, needle drivers, dissectors, graspers, or retractors. These end effectors 12 may be compliant or rigid, and may have active and passive components (depending on the motion transmission system). With reference to FIG. 16, the embodiment shown includes a compliant grasping mechanism that is at equilibrium in the open (or grasp-release) position. When the center of this grasper is pulled axially backwards, the jaws 96 of the end effector 12 close inward. In addition to grasping, the jaws 96 may have other functionality such as, but not limited to, cutting or cauterizing of tissue.

Figure 17:
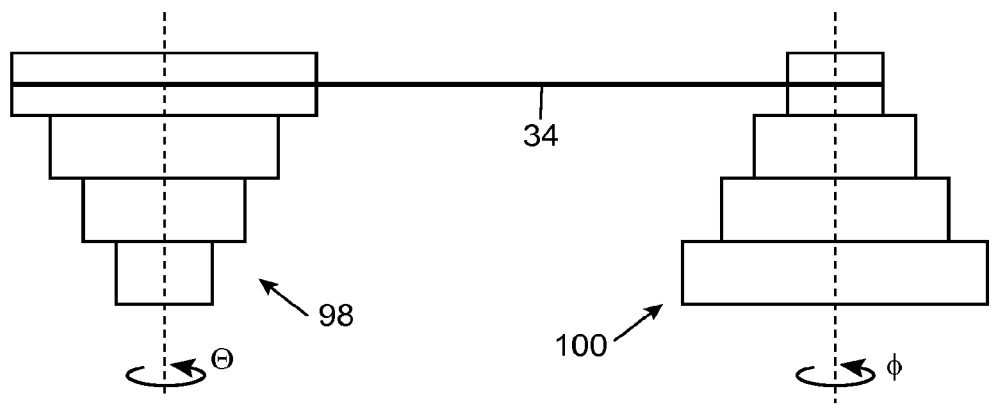
FIG. 17 is a schematic illustration of input and output pulleys allowing for a variable transmission ratio according to the present invention.
Figure 18:
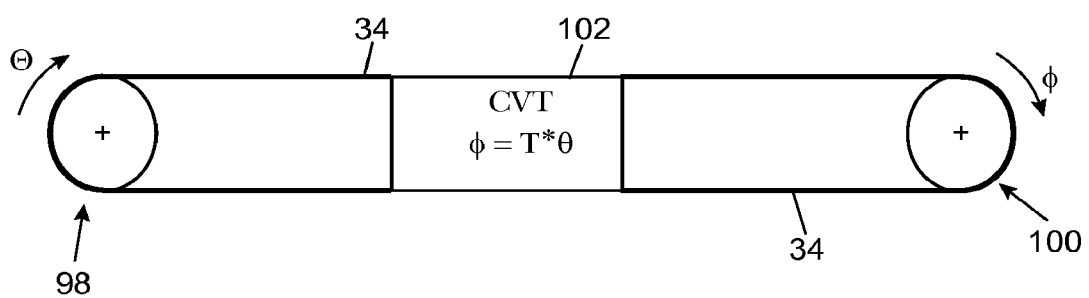
FIG. 18 is a schematic illustration of input and output pulleys allowing for a continuously variable transmission according to the present invention.

With reference now to FIG. 17, transmission between the input joint 16 and the output joint 32 may be accomplished via a pulley and cable system for each of the two wrist DoF as described with respect to several embodiments above. The design may incorporate a mechanism to scale the user's input rotation (θ) reflected at an input pulley 98 to the tool output rotation (φ) at an output pulley 100 by some transmission ratio T, thereby providing a variable transmission ratio between the tool input (user's hand rotation about his/her wrist) and tool output (end-effector 12 rotation about the output joint 32). This transmission ratio T may be fixed, may be changed in discrete steps, or may be changed continuously. Any fixed transmission ratio may be achieved by choosing appropriate radii for the input and output pulleys 98, 100. A discretely variable transmission ratio may be accomplished by means of a stepped configuration of the input and output pulleys 98, 100 such as that shown in FIG. 17, and a shifting mechanism (not shown) that allows a user to change between ratios. Alternatively, a continuously variable transmission (CVT) may be employed which allows the user to select an arbitrary ratio between input and output rotations. Such a CVT may be implemented by an intermediate module 102 such as, but not limited to, a V-Belt or toroidal arrangement, wherein a generic CVT arrangement is shown in FIG. 18. Although the CVT embodiment is illustrated in an arrangement that utilizes input and output pulleys 98, 100, it is understood that pulleys 98, 100 are not required for the implementation of a CVT in accordance with the present invention.

Figure 19:
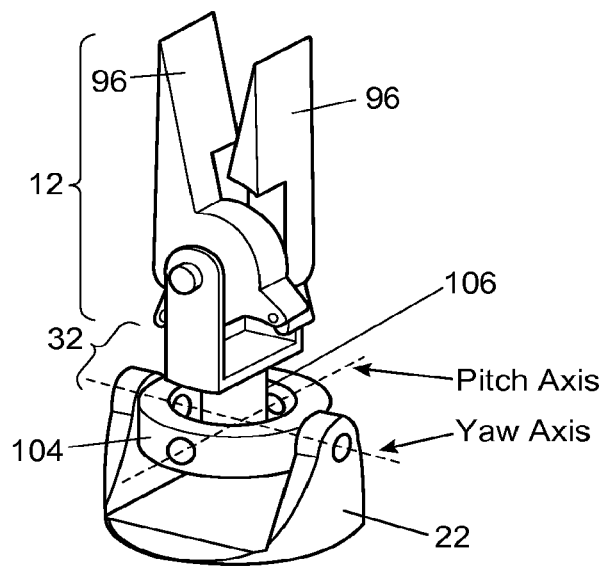
FIG. 19 is a perspective view of a tool tip manipulator and output joint according to the present invention that decouples the actuation of the two wrist DoF.

Turning next to FIG. 19, the tool 10 according to the present invention may incorporate an end-effector 12 and output joint 32 that decouple the actuation of the pitch and yaw DoF at the tool out put. As described above, the tool output comprises an end effector 12 and a 2-DoF rotational joint 32 about which the end-effector 12 can rotate. The actuation of three motions (two wrist-like rotations of the end-effector 12 about the output joint 32, and one open/close motion of the end effector jaws 96) are decoupled in this embodiment. These three motions are actuated at the input joint 16 by means of the user's hand rotation about his/her wrist, accomplished naturally via the VC mechanism 16, and an end effector actuation mechanism (e.g., lever 84 and closure mechanism 88) provided at the tool input, respectively.

Pin-based joints can achieve large rotations in very small spaces, but their mechanical implementation can result in the coupling of rotations in cascaded arrangements. In such prior art configurations, the pitch rotation of the tool is implemented after the yaw rotation and, as a result, the transmission cable actuation to produce a desired pitch depends on the current yaw angle. This is referred to as end effector motion coupling and results in non-intuitive tool output behavior. In the embodiment of the present invention depicted in FIG. 19, the output joint 32 includes a pair of nested rings 104, 106. The outer ring 104 may be connected by a pin joint to the tool shaft 22, and is actuated by a pair of cables (not shown) which may be attached to the outer ring 104 generally at the location of the pitch axis and which produce a rotation about the yaw axis. The inner ring 106 is pinned to the outer ring 104 so that the pitch axis is orthogonal to the yaw axis. The inner ring 106 is also driven by a pair of drive cables (not shown) which may be attached to the inner ring 106 at generally the same height as the outer ring 104 and generally at the location of the yaw axis. The two joints create a center of rotation acting at the intersection of the pitch and yaw axes. This arrangement prevents motion coupling by co-locating the two joint axes in an arrangement that would not be feasible with traditional cascaded, pin-based joints. This end effector 12 and output joint 32 design allows the tool 10 according to the present invention to be operated with a smaller radius of curvature, thus providing a tighter workspace which is desirable for the surgeon (user). This output joint 32 also fully separates the pitch and yaw motions to allow for completely independent motions, thus keeping the rotations mechanically decoupled.

Figure 20:
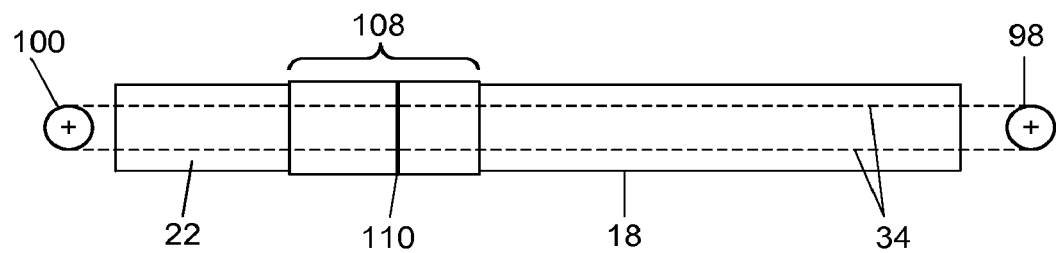
FIG. 20 is a schematic illustration of an embodiment of a minimal access tool according to the present invention which includes a quick release mechanism for replacing the tool shaft.

With reference to FIG. 20, the tool shaft 22 may be easily replaceable while the frame 18 remains attached to the user's arm. This feature allows the user to quickly replace the tool shaft 22 and end effector 12 without having to remove the entire tool 10 from his or her arm. A cable junction 108 may be provided at the connection point between the tool shaft 22 and the frame 18. Alternatively, a junction 108 may be introduced at the base of the tool frame 18, such that one part of the frame 18 that supports to the tool input remains attached to the user's forearm via the arm attachment member 20, while the rest of the frame 18 along with the tool shaft 22 is replaceable. In either of these two cases, to release and reconnect the tool shaft 22 from/to the frame 18, transmission cable connections must be severed and reconnected while maintaining sufficient cable tension to allow effective input-output motion transmission. These links could be established by a quick release mechanism 110 such as, but not limited to, a snap-fitting mechanism, magnetic coupling, or some other method of temporarily joining and releasing two tensile members. This link can be severed and reattached as desired during a surgery to allow the user to switch tool shafts 22 without having to change or remove the arm attachment member 20.

The tool 10 according to the present invention may result in significantly reduced forces at the surgical port, which in turn reduces skin/tissue trauma for the patient. In MIS tools currently on the market, placement of the tool input joint between the handle and the tool shaft makes the actuation of the tool dependent on the presence of an external ground reference, which can provide reaction loads, or in other words, close the load loop. The user applies a torque at the tool handle, and the surgical port acts as the external ground reference to provide the balancing loads necessary to allow the handle to tip downwards, which then tips the end-effector downwards. The load loop, in this case, comprises the tool handle, tool shaft, surgical port, patient's body, the ground that the patient's body rests on, the ground that the surgeon (user) stands on, the surgeon's body, the surgeon's forearm, and the surgeon's hand that grips the tool handle—in that order. As such, all the tool actuation loads necessarily flow through the surgical port and patient's body. These loads are particularly detrimental to the skin and tissue surrounding the surgical port, in the case of young or elderly patients.

In contrast, the tool 10 according to the present invention provides a common ground frame 18 that bridges the tool shaft 22 and the user's forearm. Employing the user's forearm as a ground reference locally closes the load loop associated with the wrist DoF actuation forces. Here, the load loop comprises the handle 24, the VC mechanism 16, the frame 18, the arm attachment member 20, and the user's arm and hand. Contrary to existing hand-held tools, this entirely eliminates the need for an external ground reference, such as the surgical port, to provide reaction loads.

Figure 21:
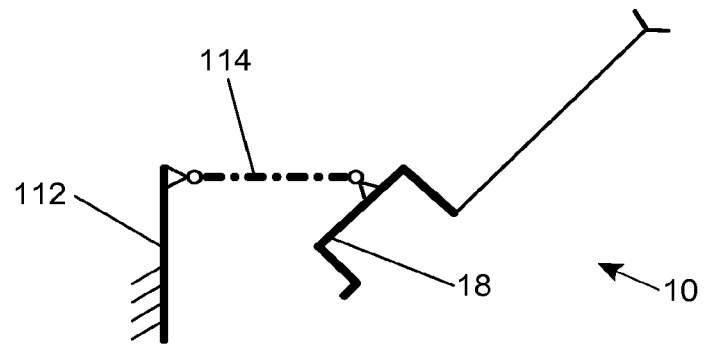
FIG. 21 is a schematic illustration of an alternative attachment of a minimal access tool according to the present invention to a support structure other than the user's forearm.

Lastly, with reference to FIG. 21, instead of the frame 18 being attached to the user's forearm, the frame 18 may be mounted on a bed frame or other structure 112 external to the user's body via an interface mechanism 114 connected therebetween which may help support the weight of the tool 10. This interface mechanism 114 may generally provide 6 DoF between the external structure 112 and the frame 18 to avoid over-constraining or limiting the motion of the tool 10. The surgeon (user) can then place his/her arm into the arm attachment member 20 and guide the tool 10 as described above while the external structure 112 supports the weight of the tool 10.

While the actuation of an end effector 12 using an input joint that may include a VC mechanism 16 is described above, in another application, a similar VC mechanism-based input joint may be used to actuate the motion of an endoscopic device. Such an arrangement would provide the user with an intuitive and ergonomic means for guiding the endoscopic device inside a patient's body.

While embodiments of the invention have been illustrated and described, it is not intended that these embodiments illustrate and describe all possible forms of the invention. It is understood that the features of various implementing embodiments may be combined to form further embodiments of the invention. The words used in the specification are words of description rather than limitation, and it is understood that various changes may be made without departing from the spirit and scope of the invention.

What is claimed is:

1. A minimal access tool, comprising:
a frame;
a tool shaft having a proximal end and a distal end, the proximal end of the tool shaft connected to the frame;
an input joint having a first end connected to the frame and a second end having a handle to receive input from a user's hand, the input joint providing articulation between the first end and the second end, the articulation comprising two orthogonal rotations, pitch rotation and yaw rotation, wherein the two orthogonal rotations correspond to two rotations associated with a wrist joint of the user holding the handle, each of the two orthogonal rotations of the articulation of the input joint being about a center of rotation that coincides with a location of articulation of the wrist joint of the user holding the handle;
the input joint comprising at least two independent mechanical paths of connection between its first end and second end, the at least two mechanical paths comprising a first mechanical path connected to the handle and to the frame and a second mechanical path connected to the handle and to the frame, wherein the first and second mechanical paths operate in parallel; and
an end effector connected to the distal end of the tool shaft via an output joint having two orthogonal rotations, wherein the output joint is coupled to the input joint via a transmission to correlate and transmit the two orthogonal rotations of the input joint to the two orthogonal rotations of the output joint, thereby transmitting the pitch rotation and yaw rotation of the wrist joint of the user holding the handle to two corresponding rotations of the output joint.

2. The tool of claim 1, wherein the frame is configured to secure to the arm of a user.

3. The tool of claim 1, wherein the transmission comprises a mechanical transmission.

4. The tool of claim 1, wherein the transmission comprises a pitch transmission cable and a yaw transmission cable routed through the tool shaft.

5. The tool of claim 1, wherein the first mechanical paths comprises a first connector having a first end coupled to the handle and having a second end coupled to the frame via a first pivot joint about a pitch rotation axis; and wherein the second mechanical path comprises a second connector having a first end coupled to the handle and having a second end coupled to the frame via a second pivot joint about a yaw rotation axis, wherein the first connector is stiff about the pitch rotation axis and is compliant about the yaw rotation axis, and wherein the second connector is stiff about the yaw rotation axis and is compliant about the pitch rotation axis.

6. The tool of claim 1, wherein the first mechanical paths comprises a first connector having a first end coupled to the handle and having a second end coupled to the frame via a first pivot joint about a pitch rotation axis; and wherein the second mechanical path comprises a second connector having a first end coupled to the handle and having a second end coupled to the frame via a second pivot joint about a yaw rotation axis, wherein the first connector is stiff about the pitch rotation axis and is compliant about the yaw rotation axis, and wherein the second connector is stiff about the yaw rotation axis and is compliant about the pitch rotation axis such that the two rotations of the input joint are decoupled into a pitch rotation only exhibited at the first pivot joint and a yaw rotation only exhibited at the second pivot joint.

7. The tool of claim 1, wherein the first mechanical paths comprises a first connector coupling the handle to the frame, wherein the first connector comprises one or more intermediate members; and wherein the second mechanical path comprises a second connector coupling the handle to the frame, wherein the second connector comprises one or more intermediate members.

8. The tool of claim 1, wherein the end effector includes jaws capable of opening and closing movements in response to a control lever disposed at the handle.

9. The tool of claim 1, wherein the first mechanical path comprises a first connector and the second mechanical path comprises a second connector, and wherein the transmission comprises a pitch pulley and a yaw pulley, wherein the pitch pulley is attached to a first end of the first connector and rotates about the pitch axis, and the yaw pulley is attached to a first end of the second connector and rotates about the yaw axis.

10. The tool of claim 1, wherein the first mechanical path comprises a first connector and the second mechanical path comprises a second connector, and wherein the transmission comprises a pitch pulley and a yaw pulley, wherein the pitch pulley is attached to a first end of the first connector and rotates about the pitch axis, and the yaw pulley is attached to a first end of the second connector and rotates about the yaw axis, and further wherein a pitch transmission cable is coupled with the pitch pulley and a yaw transmission cable is coupled with the yaw pulley.

11. A minimal access tool, comprising:
a frame;
a tool shaft having a proximal end and a distal end, the proximal end of the tool shaft connected to the frame;
an input joint having a first end connected to the frame and a second end having a handle to receive input from a user's hand, the input joint providing articulation between the first end and the second end, the articulation comprising two orthogonal rotations, pitch rotation and yaw rotation, wherein the two orthogonal rotations correspond to two rotations associated with a wrist joint of the user holding the handle;

each of the two orthogonal rotations of the articulation of the input joint being about a center of rotation such that the handle is distal with respect to this center of rotation; and the input joint comprising at least two mechanical paths of connection between the first end and the second end, the at least two mechanical paths comprising a first mechanical path connected to the handle and to the frame and a second mechanical path connected to the handle and to the frame, wherein the mechanical paths are independent and operate in parallel;

an end effector connected to the distal end of the tool shaft via an output joint having two orthogonal rotations, wherein the output joint is coupled to the input joint via a transmission to correlate and transmit the two orthogonal rotations of the input joint to the two orthogonal rotations of the output joint, thereby transmitting the pitch rotation and yaw rotation of a wrist joint of the user holding the handle to two corresponding rotations of the output joint.

12. The tool of claim 11, wherein the frame is configured to secure to the arm of a user.

13. The tool of claim 11, wherein the transmission comprises a mechanical transmission.

14. The tool of claim 11, wherein the transmission comprises a pitch transmission cable and a yaw transmission cable routed through the tool shaft.

15. The tool of claim 11, wherein the first mechanical path comprises a first connector having a first end coupled to the handle and having a second end coupled to the frame via a first pivot joint about a pitch rotation axis; and wherein the second mechanical path comprises a second connector having a first end coupled to the handle and having a second end coupled to the frame via a second pivot joint about a yaw rotation axis, wherein the first connector is stiff about the pitch rotation axis and is compliant about the yaw rotation axis, and wherein the second connector is stiff about the yaw rotation axis and is compliant about the pitch rotation axis.

16. The tool of claim 11, wherein the first mechanical path comprises a first connector having a first end coupled to the handle and having a second end coupled to the frame via a first pivot joint about a pitch rotation axis; and wherein the second mechanical path comprises a second connector having a first end coupled to the handle and having a second end coupled to the frame via a second pivot joint about a yaw rotation axis, wherein the first connector is stiff about the pitch rotation axis and is compliant about the yaw rotation axis, and wherein the second connector is stiff about the yaw rotation axis and is compliant about the pitch rotation axis such that the two rotations of the input joint are decoupled into a pitch rotation only exhibited at the first pivot joint and a yaw rotation only exhibited at the second pivot joint.

17. The tool of claim 11, wherein the first mechanical path comprises a first connector coupling the handle to the frame, wherein the first connector comprises one or more intermediate members; and wherein the second mechanical path comprises a second connector coupling the handle to the frame, wherein the second connector comprises one or more intermediate members.

18. The tool of claim 11, wherein the end effector includes jaws capable of opening and closing movements in response to a control lever disposed at the handle.

19. A minimal access tool, comprising:
a frame;
an input joint having a first end connected to the frame and a second end having a handle, the input joint providing articulation between the first end and the second end, the articulation comprising two orthogonal rotations: a pitch rotation and a yaw rotation; wherein the input joint comprises a first mechanical connector having a first end coupled to the handle and having a second end rotatably coupled to the frame about a pitch rotation axis;

a second mechanical connector having a first end coupled to the handle and having a second end rotatably coupled to the frame about a yaw rotation axis;

wherein the first mechanical connector is stiff about the pitch rotation axis and is compliant about the yaw rotation axis to transmit pitch, and wherein the second mechanical connector is stiff about the yaw rotation axis and is compliant about the pitch rotation axis to transmit yaw, and wherein pitch and yaw are transmitted independently;

a tool shaft having a proximal end and a distal end, the proximal end of the tool shaft connected to the frame;

an end effector connected to the distal end of the tool shaft via an output joint having two orthogonal rotations, wherein the output joint is coupled to the input joint via a transmission to correlate and transmit the pitch and yaw rotations of the input joint to the two orthogonal rotations of the output joint.

20. The tool of claim 19, wherein the frame is configured to secure to the arm of a user.

21. The tool of claim 19, wherein the transmission comprises a mechanical transmission.

22. The tool of claim 19, wherein the transmission comprises a pitch transmission cable and a yaw transmission cable routed through the tool shaft.

23. The tool of claim 19, wherein the end effector includes jaws capable of opening and closing movements in response to a control lever disposed at the handle.

24. A minimal access tool, comprising:
a frame;
a handle;
a first mechanical connector having a first end coupled to the handle and having a second end rotationally coupled to the frame about a first rotation axis;

a second mechanical connector having a first end coupled to the handle and having a second end rotationally coupled to the frame about a second rotation axis, wherein the first mechanical connector is stiff about the first rotation axis and is compliant about the second rotation axis, and wherein the second mechanical connector is stiff about the second rotation axis and compliant about the first rotation axis wherein the first mechanical connector and the second mechanical connector operate independently;

a tool shaft having a proximal end and a distal end, the proximal end of the tool shaft connected to the frame;

an end effector connected to the distal end of the tool shaft via an output joint having two rotations, wherein the output joint is coupled to the input joint via a transmission connected therebetween to correlate and transmit the rotation of the second end of the first mechanical connector and the rotation of the second end of the second mechanical connector to the two rotations of the output joint.

25. The tool of claim 24, wherein the first rotation axis comprises pitch rotation and the second rotation axis comprises yaw rotation.

26. The tool of claim 24, wherein the frame is configured to secure to the arm of a user.

27. The tool of claim 24, wherein the transmission comprises a mechanical transmission.

28. The tool of claim 24, wherein the end effector includes jaws capable of opening and closing movements in response to a control lever disposed at the handle.

29. A minimal access tool, comprising:
a frame;
a handle having two orthogonal rotations, pitch rotation and yaw rotation, with respect to the frame;
a first mechanical connector having a first end coupled to the handle and having a second end coupled to the frame via a first pivot joint about a pitch rotation axis;
a second mechanical connector having a first end coupled to the handle and having a second end coupled to the frame via a second pivot joint about a yaw rotation axis,
wherein the first mechanical connector is stiff about the pitch rotation axis and is compliant about the yaw rotation axis to transmit pitch, and wherein the second mechanical connector is stiff about the yaw rotation axis and is compliant about the pitch rotation axis to transmit yaw,
wherein the pitch and yaw rotation axes are orthogonal to each other, and
wherein the first mechanical connector and the second mechanical connector are independent and operate in parallel.

30. The tool of claim 29, wherein the first mechanical connector couples the handle to the frame via a first plurality of pivotally linked intermediate members; and wherein the second mechanical connector couples the handle to the frame via a second plurality of pivotably linked intermediate members.

31. The tool of claim 29, wherein the first mechanical connector and the second mechanical connector decouple the two orthogonal rotations of the handle relative to the frame into a pitch rotation exhibited only at the first pivot joint and a yaw rotation exhibited only at the second pivot joint.

* * * * *